United States Patent [19]

Glowczewskie, Jr. et al.

[11] Patent Number: 4,994,030

[45] Date of Patent: Feb. 19, 1991

[54] RECONSTITUTION OF HUMAN BONE AND TISSUE

[75] Inventors: Frank P. Glowczewskie, Jr., Gainesville, Ill.; David A. Present, New York, N.Y.; David W. Anderson, New York, N.Y.; Patrick A. McBrayer, Yardley, Pa.

[73] Assignee: Osteotech, Inc., Shrewsbury, N.J.

[21] Appl. No.: 212,516

[22] Filed: Jun. 28, 1988

[51] Int. Cl.⁵ .............................................. A61M 37/00
[52] U.S. Cl. ........................................ 604/84; 604/413
[58] Field of Search .................. 623/16; 604/82–88, 604/411–413, 416

[56] References Cited

U.S. PATENT DOCUMENTS 3,458,397  7/1969  Myers et al. .................... 623/16 X
3,542,023  11/1970  Ogle ................................. 604/88
4,442,655  4/1984  Stroetmann .................... 623/16 X Primary Examiner—Alan W. Cannon
Attorney, Agent, or Firm—Dilworth & Barrese

[57] ABSTRACT

A kit and process for reconstituting human bone and/or related tissue is disclosed. The kit comprises a pre-formulated sterilized reconstitution medium and double ended transfer needle.

5 Claims, 2 Drawing Sheets

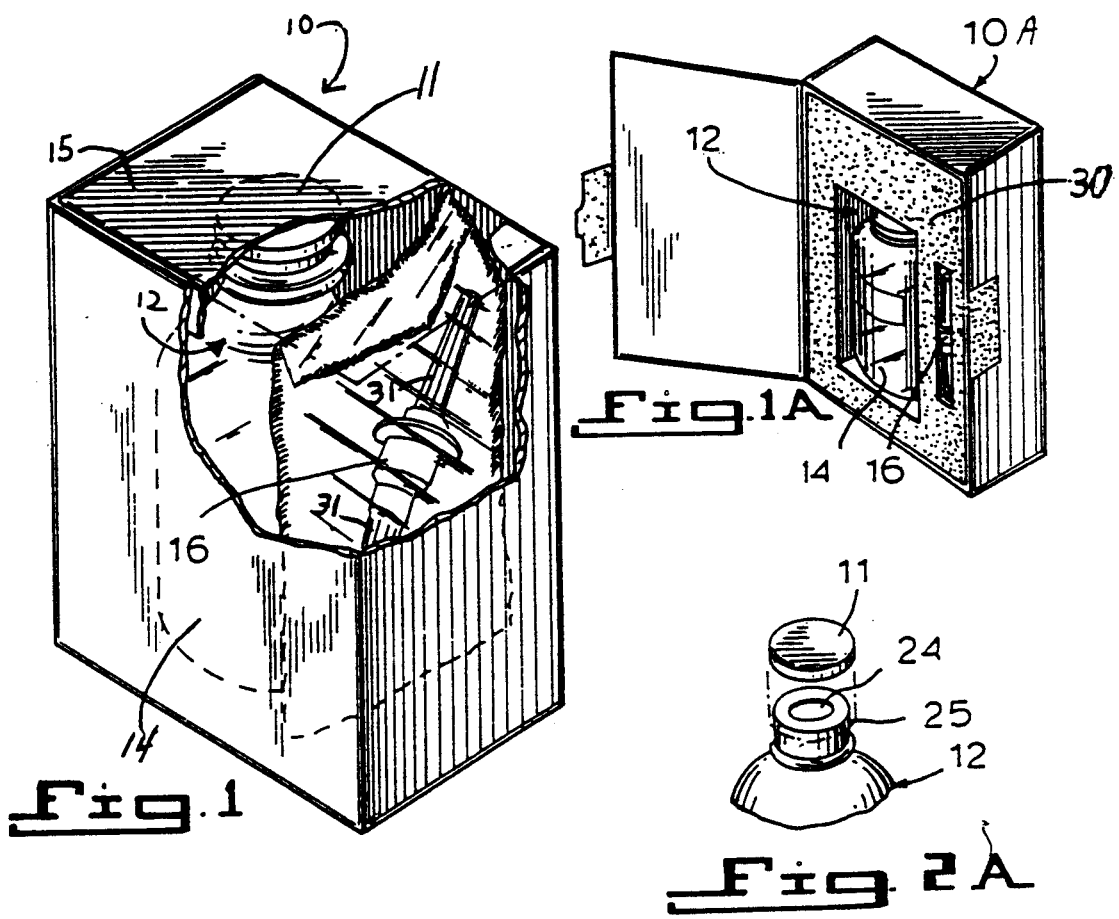
Fig. 1
Fig. 1A
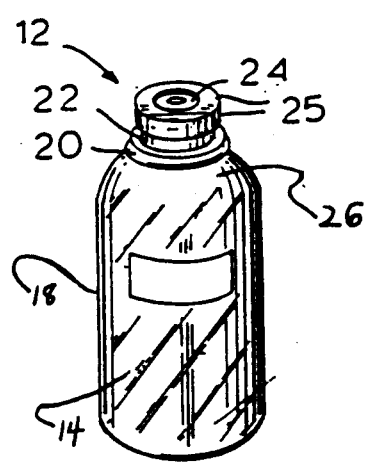
Fig. 2
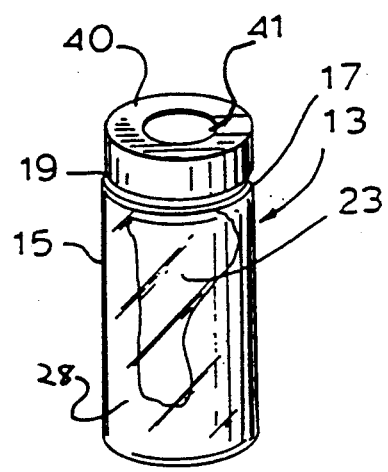
Fig. 3

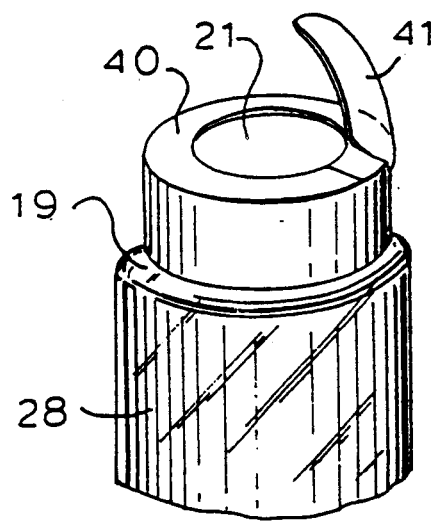
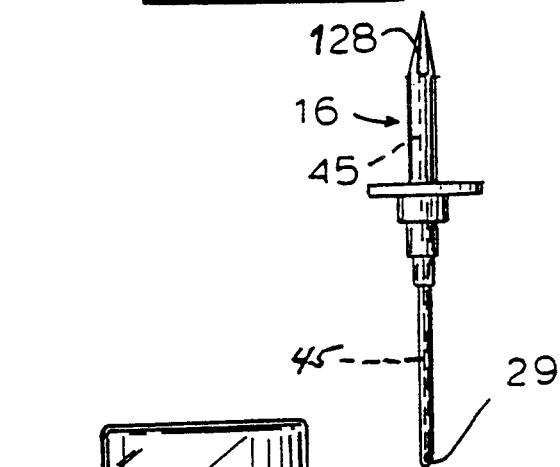
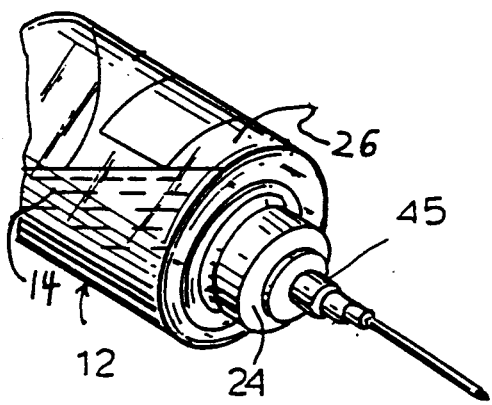
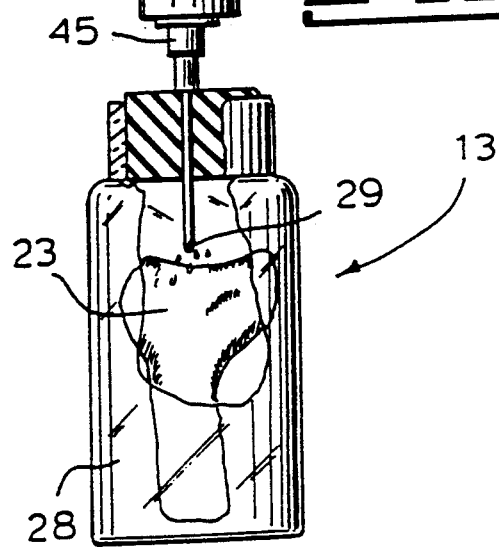

4,994,030

RECONSTITUTION OF HUMAN BONE AND TISSUE

BACKGROUND OF THE INVENTION

This invention relates to the reconstitution (rehydration) of human bone and other related allograft tissue and more particularly to a kit and process for the reconstitution of freeze-dried human bone and musculoskeletal allograft tissue.

The concept and procedure of human organ transplants has gained wide acceptance in the medical community as a viable manner to treat human disorders which would otherwise be untreatable. A currently expanding medical procedure involves the transplanting of human allograft bone and related allograft tissue, extracted from recently deceased human cadavers, to recipients in need of such bone and tissue.

In order to provide allograft bone and related tissue which is suitable for transplanting, such bone and tissue must be recovered in operating rooms under sterile conditions and moreover must be processed and stored under specific aseptic guidelines. In order to preserve the biologic and biomechanical integrity of the bone or tissue, the bone or tissue is typically freeze-dried and stored as such. However, prior to its intended use as a transplant organ, freeze-dried human bone or tissue requires reconstitution under aseptic/sterile conditions.

In the past, reconstitution procedures involved a laborious and uncontrolled multi-step process to ensure that the bone or tissue remains sterile during the procedure. Generally, past procedures require the preparation of a reconstitution solution comprised of sterile water to which antibiotics are added as a preservative. Antibiotic preservative is required since typically several hours of reconstitution may be necessary to obtain bone or tissue suitably pliable for pre-operative shaping and incubation of the bone or tissue in sterile water alone cannot be expected to reliably maintain sterility of the bone or tissue over the entire reconstitution period.

In the past, the selection of the types and quantities of antibiotics employed has been left, for example, to the surgical team. In some instances, this selection may not be optimal for the maintenance of sterility and/or protection of the transplant recipient. Furthermore, it may be necessary to transfer the bone or tissue and/or reconstitution medium to another container of variable suitability for the period of reconstitution As a final step, the bone or tissue is rinsed with sterile water to remove any traces of antibiotic just prior to transplantation.

It is, therefore, readily apparent that past procedures for the reconstitution of bone or other musculoskeletal allograft tissue lack the convenience and uniformity to assure that sterile technique and recipient safety are being maintained. Therefore, an improved reconstitution procedure is highly desired.

SUMMARY OF THE INVENTION

Accordingly, it is one object of the present invention to provide a kit useful for the reconstitution of human bone and/or human allograft tissue.

Another object of this invention is to provide an improved process for the reconstitution of human bone and/or allograft tissue.

A further object of the present invention is to provide a controlled and convenient process for the reconstitution of human bone and/or tissue which ensures uniformity of method and minimal handling of the bone and/or tissue, thereby improving the maintenance of sterility.

These and other objects are accomplished herein by providing a kit for reconstituting human bone and/or tissue, said kit comprising:

(a) a sealed vessel containing a pre-formulated reconstitution medium for human bone and/or tissue, said sealed vessel comprising an access site into the interior of the vessel; and (b) means for accessing the interior of said sealed vessel and for placing the interior of said sealed vessel in open communication with a sealed vessel containing human bone and/or tissue necessitating reconstitution.

Other objects of the invention are accomplished herein by a process for reconstituting human bone and/or tissue, said process comprising the steps of:

(a) providing a first sealed vessel containing a pre-formulated reconstitution medium, said sealed vessel comprising an access site into the interior of the vessel;

(b) providing a second sealed vessel containing bone and/or tissue necessitating reconstitution, said sealed vessel comprising an access site into the interior of the vessel;

(c) providing a means for accessing the interiors of said first and second sealed vessels and a flow path means for placing the interiors of the said first and second sealed vessels in open communication with each other;

(d) accessing the interiors of said first and second sealed vessels with the accessing means recited in step (c) at said access sites of said first and second sealed vessels, thereby providing an open flow path between said first and second sealed vessels; and (e) passing said pre-formulated reconstitution medium from said first sealed vessel through said open flow path and into the interior of said second sealed vessel thereby reconstituting said bone and/or tissue contained in said second sealed vessel.

BRIEF DESCRIPTION OF THE DRAWINGS

FIG. 1 is a perspective view (cut-away) of a convenient package in which the components of the kit of the present invention may be stored;

FIG. 1A illustrates another package in which the components of the kit of the present invention may be stored;

FIG. 2 is a perspective view of a sealed vessel containing a pre-formulated liquid reconstitution medium in accordance with the present invention;

FIG. 2A depicts the upper portion of the sealed vessel of FIG. 2 and further illustrates a protective flip-off cap (shown removed) which typically covers the top of the vessel prior to use;

FIG. 3 is a perspective view of a sealed vessel containing freeze-dried bone;

FIG. 4 is an upper portional view of the sealed vessel of FIG. 3 after the pull back tab has been removed;

FIG. 5 is a perspective view of a double-pointed-ended transfer needle employed in the kit and process of the present invention; and FIG. 6 is an illustration of one step in the reconstitution process of the present invention.

FIG. 7 is a further illustration of the reconstitution process of the present invention.

DETAILED DESCRIPTION OF THE INVENTION

Figure 12:
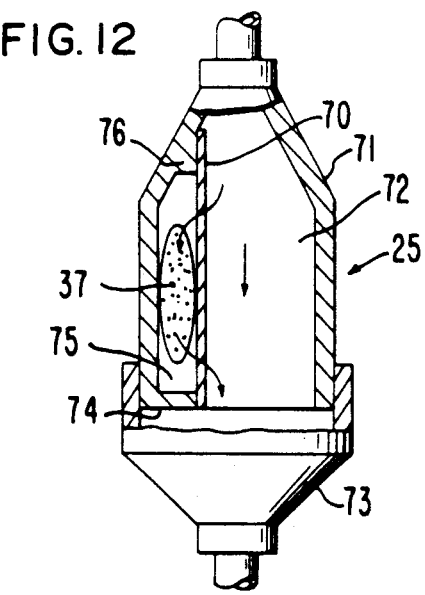
Figure 13:
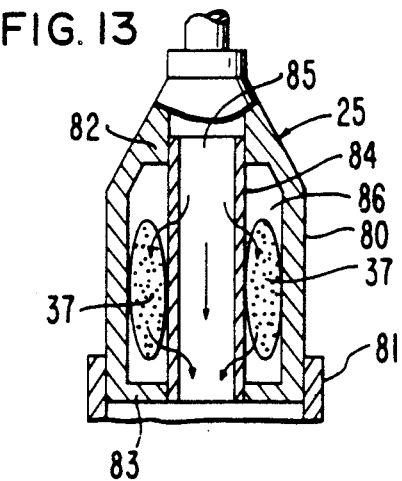
Figure 14:
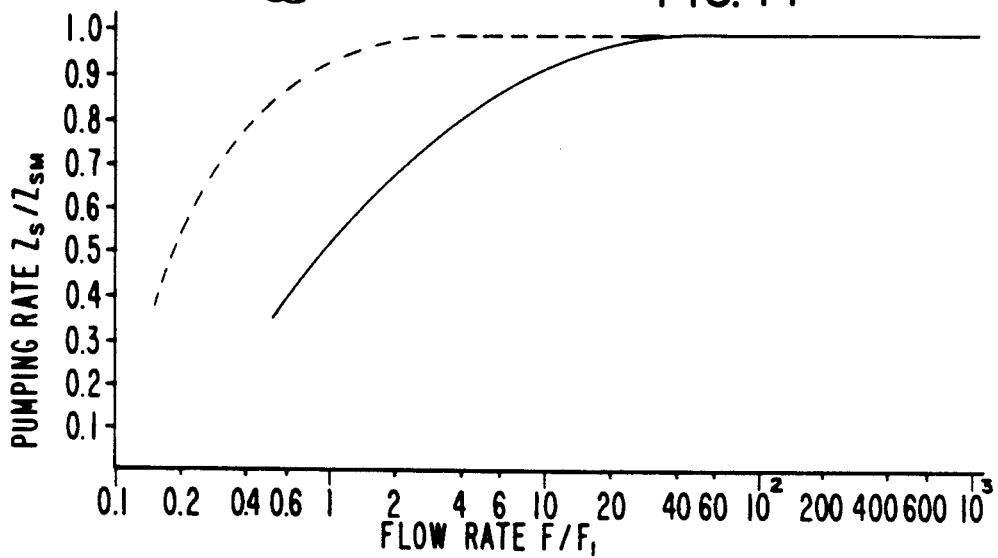
Figure 15:
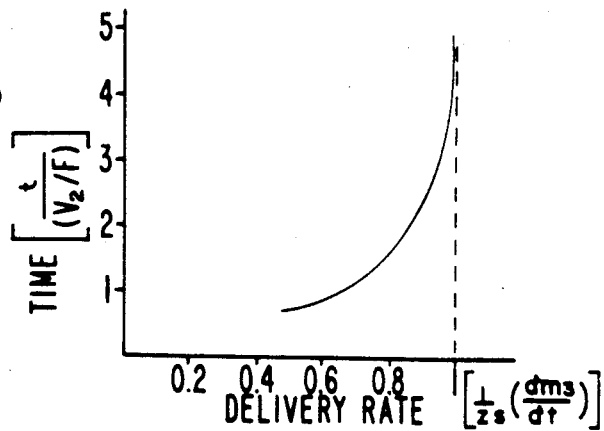

FIG. 1 illustrates a package 10, typically constructed from paperboard and having a conventional opening and closing flap 15 at one end thereof, in which the components of the kit of the present invention are stored. In particular, package 10 contains aseptically sealed vessel 12 containing a sterile pre-formulated liquid reconstitution medium 14 and an aseptically wrapped sterile double ended transfer needle 16 having protective and safety caps or sheaths 31. FIG. 1A illustrates another embodiment of a package 10A in which the components of the kit of the present invention may be stored. Package 10A may be also constructed of paperboard and has a foam insert 30 which is fashioned to hold sealed vessel 12 and transfer needle 16.

As shown in FIG. 2, sealed vessel 12 may be of standard construction as employed in the pharmaceutical and medical industry, such as a vial. For example, vessel 12 is typically constructed of transparent glass and includes a body 18, a neck 20 and a mouth 22. A rubber or other resilient stopper 24 is snugly mounted within the vessel mouth 22. The rubber stopper 24 serves as an access site into the interior chamber 26 of the vessel. For the purposes of the present invention, the size of vessel 12 is preferably about 100 ml. in volume, although smaller or larger volume vessels are obviously contemplated herein.

Furthermore, as illustrated in FIG. 2, the vessel 12 typically includes a metal, such as aluminum or other metal, malleable band 25 mounted about the outer perimeter of the upper portion of the mouth 22 and partially covering the stopper 24, thereby assisting to retain the stopper 24 within the vessel 12.

Moreover, as shown in FIG. 1 and FIG. 2A, the sealed vessel 12 is typically provided with a protective flip-off or pull-off cap 11 (shown removed in FIG. 2A) covering the top surface of stopper 24 and top surface of band 25.

The aseptically sealed vessel 13, containing the freeze-dried bone or other freeze-dried allograft tissue necessitating reconstitution, illustrated in FIG. 3, is constructed similarly to vessel 12 of FIG. 2. That is, like vessel 12, aseptically sealed vessel 13 is typically constructed of transparent glass and includes a body 15, a neck 17 and a mouth 19. A rubber or other resilient stopper 21 is snugly mounted within the vessel mouth 19 and overfitted with a metallic, pull away cap 40 having a pull away tab 41 as depicted by FIG. 4. The rubber stopper 21 serves as an access site into the interior chamber 26 of the vessel containing the freeze-dried bone or tissue 23.

Sealed vessel 13, like sealed vessel 12, typically includes a metal, such as aluminum or other metal, malleable band mounted about the outer perimeter of the mouth 19 and the stopper 21, thereby assisting to retain the stopper 21 within the vessel 13.

FIG. 5 illustrates the sterile, double open ended, hollow transfer needle 16 provided in the kit of the present invention and which is employed in the reconstituting process of the present invention. The needle 16 includes two sharp, piercing, pointed opposite open ends 128 and 29 in open flow communication with each other. Thus, in a preferred embodiment the transfer needle 16 embodies means for entering the sealed vessel 12 through the pointed end 128, means for entering the interior of the sealed vessel 13, through the pointed end 29, and flow path means 45 for placing the interiors of the sealed vessels 12 and 13 in open communication. Other accessing means and flow path means are also within the scope of the present invention, the needle 16 being a preferred embodiment. As depicted in FIG. 5, the transfer needle is shown wherein the portion comprising open end 128 is shorter in length and of a larger diameter than the needle portion comprising open end 29. Furthermore, as depicted in FIG. 5, the portion of the needle comprising open end 128 has as a spike configuration, for example, constructed of plastic, while the portion comprising open end 29 is constructed of, for example, stainless steel and is of typical needle configuration While FIG. 5 represents a preferred transfer needle, others are also suitable for the purposes of this invention. Thus, for example, the lengths, diameters and thicknesses of the needles comprising the pointed ends need only be sufficient to penetrate and fully pass through the stoppers of the respective vessels. Rigid, double pointed open ended transfer needles, such as that depicted in FIG. 5, are conventional and are readily commercially available. For example, a preferred transfer needle for purposes of the present invention is sold by Burron Medical Inc., Bethlehem, Penna.

The manner in which the reconstituting process of the present invention is carried out utilizing the kit of the present invention is illustrated by FIGS. 6 and 7, wherein it is shown that the needle end 128 is inserted through the stopper 24 of sealed vessel 12 thereby accessing the interior 26 of vessel 12 and the opposite end 29 of needle 16 is inserted into the stopper 21 of sealed vessel 13 thereby accessing the interior 28 of vessel 13. Typically, the stoppers of both vessels 12 and 13 are wiped with an aseptic cleansing agent, such as betadine or ethyl alcohol before being pierced with needle 16. Generally, the freeze-dried bone or tissue has been sealed in vessel 13 under vacuum and as such the transfer or passing of the reconstitution medium from vessel 12 to vessel 13 through the open flow path provided by hollow transfer needle 16 proceeds very readily. However, notwithstanding the presence of a vacuum in sealed vessel 13, the transfer of the liquid reconstitution medium from sealed vessel 12 to sealed vessel 13 still proceeds very readily under normal gravitational conditions in accordance with the present process as described and illustrated herein. Preferably, sealed vessel 13 should be positioned so that the reconstitution medium completely covers the freeze-dried bone or tissue.

The reconstitution medium 14 contained in sealed vessel 12 of the present invention preferably comprises a sterile aqueous solution of a preservative. Suitable preservatives for purposes of the present invention include materials which are effective in inhibiting contamination of the human bone or related tissue by common microorganisms. Generally, suitable preservatives are, for example, antibiotics and other bactericides and/or bacteriostats. A preferred preservative for the purposes herein is the antibiotic gentamicin sulfate. Other suitable bactericides useful as preservatives herein include, for example, bacitracin, polymyxin B, neomycin, cefazolin sodium. Suitable amounts of preservative for purposes of the present invention are generally those amounts and concentrations which are suitable to preserve the sterility of the bone or tissue during the reconstitution and subsequent implant procedure. Thus, for example, suitable preservative concentrations for the preferred reconstitution solution of the present invention, which utilizes gentamicin sulfate, are typically in the range of from about 250 to about 1000 micrograms/ml, preferably from about 400 to about 750 micrograms/ml and most preferably about 500 micrograms/ml.

Generally, the total volume of the reconstitution solution contained in vessel 12 is sufficient to allow for completely covering the freeze-dried bone or tissue contained in vessel 13. Typically, for example, vessel 12 will contain 75 ml of pre-formulated reconstitution solution, although greater or smaller amounts are also within the practice of this invention.

It is generally recommended that the bone or tissue be reconstituted for a minimum of about one hour at room temperature before use. If the bone or tissue is to be shaped, drilled or cut, longer periods of incubation may be necessary or desirable to increase bone or tissue pliability. Bone or tissue to be incubated for longer than two hours is generally stored at about 4°-8° C. Upon completion of the reconstitution process, the selected tissue is generally rinsed with sterile water just prior to implantation.

While several embodiments and features have been described in detail herein and shown in the accompanying drawings, it will be evident that various further modifications are possible without departing from the scope of the invention.

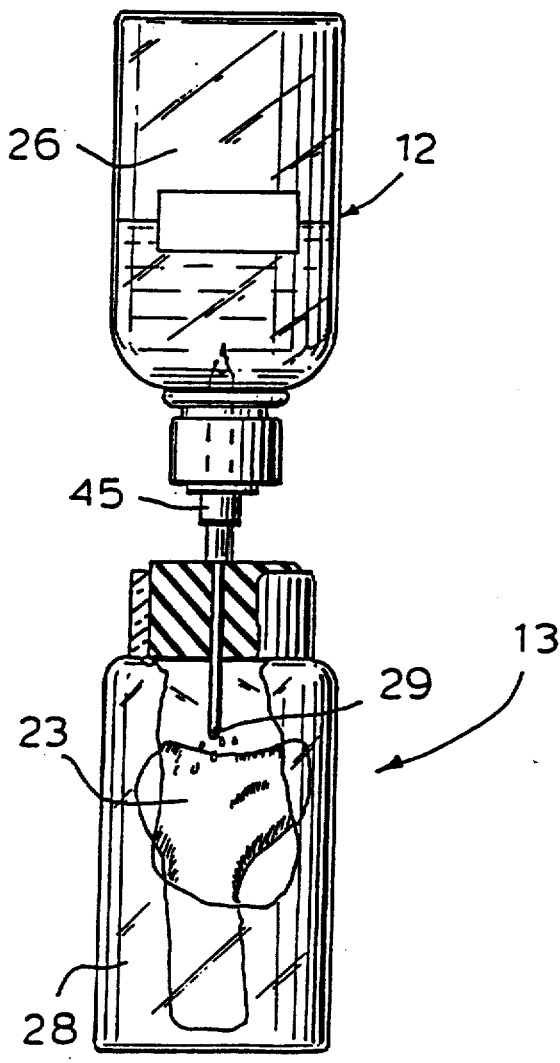

What is claimed is:

1. A kit for reconstituting human tissue selected from the group consisting of bone and musculoskeletal tissue, said kit comprising:
    (a) a sealed vessel containing a sterile preformulated reconstitution medium for said human tissue, said sealed vessel comprising an access site into the interior of said vessel; and
    (b) means for accessing the interior of said sealed vessel and for placing the interior of said vessel in open communication with the interior of a sealed vessel containing said human tissue necessitating reconstitution;
    wherein said pre-formulated reconstitution medium comprises a sterile aqueous solution including, in an amount suitable to preserve sterility of said human tissue during reconstitution and subsequent implant, a preservative selected from the group consisting of gentamicin sulfate, bacitracin, polymyxin B, neomycin and cefazolin sodium; and
    said means of accessing the interior of said sealed vessel comprises a hollow needle having two opposite pointed open ends and being separate from both said sealed vessel containing said reconstitution medium and said sealed vessel containing said human tissue.

2. The kit according to claim 1 wherein said sealed vessel containing said sterile pre-formulated reconstitution medium comprises a vial having a mouth aseptically sealed with a snugly fitting stopper means, said stopper means providing said access site into the interior of said vessel.

3. The kit according to claim 2 wherein said snugly fitting stopper means is a rubber stopper.

4. A kit for reconstituting human tissue selected from the group consisting of bone and musculoskeletal tissue, said kit comprising:
    (a) a sealed vessel containing a sterile preformulated reconstitution medium for said human tissue, said sealed vessel comprising an access site into the interior of said vessel;
    (b) means for accessing the interior of said sealed vessel and for placing the interior of said vessel in open communication with the interior of a sealed vessel containing said human tissue necessitating reconstitution;
    wherein said pre-formulated reconstitution medium comprises a sterile aqueous solution of gentamicin sulfate having a concentration of from about 250 to about 1000 micrograms/ml.; and
    said means of accessing the interior of said sealed vessel comprises a hollow needle having two opposite pointed open ends and being separate from both said sealed vessel containing said reconstitution medium and said sealed vessel containing said human tissue.

5. The kit according to claim 4 wherein said sterile aqueous solution of gentamicin sulfate has a concentration of about 500 micrograms/ml.

* * * * *

UNITED STATES PATENT AND TRADEMARK OFFICE
CERTIFICATE OF CORRECTION

PATENT NO. : 4,994,030　　　　　　　　　　　　　　　　Page 1 of 2

DATED : 2/19/91

INVENTOR(S) : Glowczewskie, Jr. et al

It is certified that error appears in the above-identified patent and that said Letters Patent is hereby corrected as shown below:

The title page should be deleted to appear as per attched title page.

Signed and Sealed this

Third Day of November, 1992

Attest:

DOUGLAS B. COMER

Attesting Officer　　　　　　　　Acting Commissioner of Patents and Trademarks

United States Patent [19]
Glowczewskie, Jr. et al.

[11] Patent Number: 4,994,030
[45] Date of Patent: Feb. 19, 1991

[54] RECONSTITUTION OF HUMAN BONE AND TISSUE

[75] Inventors: Frank P. Glowczewskie, Jr., Gainesville, Ill.; David A. Present, New York, N.Y.; David W. Anderson, New York, N.Y.; Patrick A. McBrayer, Yardley, Pa.

[73] Assignee: Osteotech, Inc., Shrewsbury, N.J.

[21] Appl. No.: 212,516

[22] Filed: Jun. 28, 1988

[51] Int. Cl.⁵ ............................................. A61M 37/00
[52] U.S. Cl. ........................................ 604/84; 604/413
[58] Field of Search ................... 623/16; 604/82–88, 604/411–413, 416

[56] References Cited

U.S. PATENT DOCUMENTS

| | | | |
|---|---|---|---|
| 3,458,397 | 7/1969 | Myers et al. | 623/16 X |
| 3,542,023 | 11/1970 | Ogle | 604/88 |
| 4,442,655 | 4/1984 | Stroetmann | 623/16 X |

Primary Examiner—Alan W. Cannon
Attorney, Agent, or Firm—Dilworth & Barrese

[57] ABSTRACT

A kit and process for reconstituting human bone and/or related tissue is disclosed. The kit comprises a pre-formulated sterilized reconstitution medium and double ended transfer needle.

5 Claims, 2 Drawing Sheets